United States Patent
Carroll

(10) Patent No.: US 6,470,891 B2
(45) Date of Patent: Oct. 29, 2002

(54) PHOTOCHROMATIC TATTOO

(76) Inventor: George H. Carroll, 3033 Grove Ave., Ventura, CA (US) 93003

( * ) Notice: Subject to any disclaimer, the term of this patent is extended or adjusted under 35 U.S.C. 154(b) by 0 days.

(21) Appl. No.: 09/459,099

(22) Filed: Dec. 13, 1999

(65) Prior Publication Data

US 2002/0074003 A1 Jun. 20, 2002

(51) Int. Cl.$^7$ ............................................. A61B 19/00
(52) U.S. Cl. ...................................................... 128/897
(58) Field of Search ................................ 128/897, 898; 424/400, 401, 59, 60; 382/115, 116, 124–127, 100, 128, 133; 348/15, 77, 161; 209/3.3, 555; 106/31.03, 31.15, 31.32

(56) References Cited

U.S. PATENT DOCUMENTS

| | | | | |
|---|---|---|---|---|
| 5,017,225 A | 5/1991 | Nakanishi | ................... | 106/21 |
| 5,028,792 A | 7/1991 | Mullis | ................... | 250/474 |
| 5,074,306 A | 12/1991 | Green | ................... | 128/664 |
| 5,085,607 A | 2/1992 | Shibahashi | ................... | 446/14 |
| 5,166,345 A | 11/1992 | Akashi | ................... | 544/71 |
| 5,176,905 A | 1/1993 | Ohno | ................... | 424/69 |
| 5,383,959 A | 1/1995 | Sirdesai | ................... | 106/21 |
| 5,436,115 A | 7/1995 | Mullis | ................... | 430/338 |
| 5,465,524 A | 11/1995 | Vallone | ................... | 43/42.32 |
| 5,516,362 A | 5/1996 | Gundjian | ................... | 106/22 |
| 5,581,090 A | 12/1996 | Goudjil | ................... | 250/474 |
| 5,633,109 A | 5/1997 | Jennings | ................... | 430/115 |
| 5,730,961 A | 3/1998 | Goudjil | ................... | 424/61 |
| 5,762,913 A | 6/1998 | Tanaka | ................... | 424/59 |
| 5,795,379 A | 8/1998 | Schwenk | ................... | 106/499 |
| 5,878,155 A | 3/1999 | Heeter | ................... | 382/115 |
| 6,013,122 A | * 1/2000 | Klitzman et al. | ................... | 106/31.03 |
| 6,080,415 A | * 6/2000 | Simon | ................... | 424/59 |

* cited by examiner

Primary Examiner—Kevin Shaver
Assistant Examiner—Brian Szmal
(74) Attorney, Agent, or Firm—Dennis H. Lambert

(57) ABSTRACT

A tattoo that is invisible to the naked eye until the tattoo is exposed to ultraviolet radiation, whereupon the tattoo becomes visible to the naked eye, and which reverts to invisible upon removal from exposure to ultraviolet radiation. The tattoo is formed by embedding in the skin a mixture including a non-pigmented carrier and one or more photochromic compounds that undergo a photochemical transformation from colorless to colored upon exposure to ultraviolet radiation, and which revert to colorless upon removal from exposure to ultraviolet radiation.

6 Claims, No Drawings

PHOTOCHROMATIC TATTOO

BACKGROUND OF THE INVENTION

1. Field of the Invention

This invention relates generally to tattoos. More particularly, this invention relates to a tattoo that normally is not visible to the naked eye, but which becomes visible upon exposure to a source of ultraviolet radiation, such as sunlight or an ultraviolet lamp.

2. Prior Art

The art of tattooing has been known for many years. Traditional tattoos are applied by using needles or needle-like instruments to inject colored ink or dyes into the skin of the person receiving the tattoo. Consequently, traditional tattoos are permanent in nature and may be removed only with difficulty, if they may be removed at all. However, in many instances persons act impulsively when they have a tattoo applied. Because of changed circumstances, or for other reasons these persons may later change their mind, and may wish to have the tattoo removed or altered.

Moreover, even if a person continues to be satisfied with the tattoo and proudly displays it, there may be occasions when a tattoo is not appropriate or the person may otherwise then wish to not display it. In such instances, the person has little choice except to cover the tattoo with clothing, which itself may be inappropriate, or attempt to have the tattoo otherwise obscured or removed from sight.

At least partially because of these difficulties, temporary tattoos, or even jewelry that superficially appears as a tattoo, have been developed so that a person can apply a tattoo to be temporarily worn and then removed by washing, etc. However, the appeal of these temporary tattoos is limited by the fact that they are generally available only in predetermined designs, and the tattoo typically comes off when it becomes wet. Moreover, it may bleed onto clothing.

Accordingly, there is need for a permanent or semi-permanent tattoo that does not wash off in water and which will not bleed onto clothing, but which is not visible unless desired.

SUMMARY OF THE INVENTION

The invention provides a tattoo that is permanent or semi-permanent, does not wash off or bleed on clothes, and remains invisible until the wearer desires it to be seen.

More particularly, the invention comprises a photochromatic tattoo in which photochromic compounds normally invisible to the naked eye, but which become visible upon exposure to sunlight or other sources of ultraviolet radiation (UV), are embedded in the skin to create a tattoo. The photochromic compounds are mixed in a non-pigmented or clear carrier that is substituted for the normal pigmented ink or dye that is used to apply a tattoo. The tattoo thus remains invisible to the naked eye until it is exposed to UV.

Examples of suitable photochromic compounds are described in U.S. Pat. Nos. 5,581,090 and 5,730,961, the disclosures of which are incorporated in full herein by reference. As noted in the '090 and '961 patents, photochromic substances are known in the art for their utilization in optics as storage media or as a means to detect UV, such as, e.g., the photochromic ultraviolet detector disclosed in the '090 patent. Among the large family of photochromic compounds are the spiropyrans and spiroxazines groups of molecules. These molecules are known for their property of changing from clear to a variety of colors and shades. Normally appearing as colorless, these spiro-compounds undergo a photochemical transformation to intensely colored form when exposed to UV. The '961 patent, in particular, discloses a material which remains clear until exposed to UV and which then exhibits color and thus becomes visible. The active chemical disclosed in the '961 patent is identified as a photochromic substance such as spiropyrans or spiroxazines molecules. However, this patent relates to a nail polish applied to the surface of the nails of a wearer, and does not relate to a tattoo applied transdermally to the skin of the wearer.

A carrier for the photochromic compounds could comprise an invisible skin-marking ink such as that made by Sirchie Finger Print Laboratories of Youngsville, N.C., under the name "Invisible Skin Marking Ink #743", and described more fully in U.S. Pat. No. 5,878,155. However, other suitable commercially available, transparent, non-toxic carriers could be used to embed the photochromic compounds in the skin.

U.S. Pat. No. 5,166,345 describes a photochromic compound which exhibits high color density, is stable against heat and solvent, and which has a great repeating durability in coloring-decoloring cycles. For improved performance, the photochromic compound used to produce a tattoo in accordance with the present invention can be formulated using the teachings of this patent, the disclosure of which is incorporated in full herein, whereby the stability, durability and color intensity, for example, of the compound are optimized.

Further, the composition used to make the photochromatic tattoo of the invention may be formulated so that it is operative only for a predetermined period of time, e.g., days, weeks or months, etc., after which the photochromic composition is no longer effective to produce a visible tattoo when exposed to UV. Alternatively, or in addition, the composition may be formulated so that once exposed to UV, the tattoo will remain visible only for a predetermined period of time, e.g., minutes, hours or days, etc.

DETAILED DESCRIPTION OF THE PREFERRED EMBODIMENTS

The tattoo of the present invention is invisible to the naked eye until the tattoo is exposed to sunlight or other source of ultraviolet radiation, at which time the tattoo undergoes a photochemical change from clear or colorless to intensely colored, thereby producing a visible tattoo. Upon removal from exposure to UV, the tattoo again becomes invisible. By appropriate formulation, the tattoo can be made to return to clear and therefore become invisible almost immediately, or following a predetermined desired period of time.

To produce the tattoo of the invention, a photochromic compound is mixed with a suitable carrier, such as the ink disclosed in U.S. Pat. No. 5,878,155, for example, and embedded in the skin by utilizing conventional tattooing methods. The photochromic compound is preferably selected from the spiropyrans and spiroxazine groups of the photochromic family of compounds, such as those disclosed in U.S. Pat. 5,581,090, for example. The spiropyrans and spiroxazine compounds normally appear as colorless but undergo photochemical transformation and exhibit intense colors when exposed to UV radiation.

The spiropyrans or spiroxazine compounds may be added to the carrier in a proportion of about 0.1 to about 1.0 percent by weight. Higher concentrations yield more intense colors. Different color hues are obtained by mixing two or more spiropyrans or spiroxazine compounds in the carrier, as necessary or desired.

During application of the tattoo, it is necessary to expose the area being tattooed to UV radiation so that the design is visible to the tattooist. Upon exposure to UV radiation from a lamp or sunlight, for example, the tattoo becomes fully visible after only about five (5) seconds.

A commercially available stabilizer may be added to the composition to reduce oxidation processes and thereby extend the useful life of the photochromic compound. Commercially available stabilizers suitable for their performance under sunlight are Tinuvin 765 and Tinuvin 144 Hindred Amine Light Stabilizers, available from the Additive Division of Ciba Geigy. The stabilizers may be added in a proportion of from about 2.5% up to about 3.0% by weight.

The photochromatic tattoo of the invention can be applied using conventional tattooing methods and equipment, and when visible appears as a conventional tattoo. It can have the permanence, individuality, artistry and intricate detail of a conventional tattoo, but remains invisible until exposed to UV radiation. Thus, the person wearing the tattoo can dress in formal clothing or swim wear, etc., without displaying the tattoo, and when desired can activate the tattoo for display simply by exposing it to UV radiation. If desired, the tattoo can even be made to remain invisible when the person wearing the tattoo is exposed to sunlight or other source of UV radiation by covering the tattoo with an appropriate sun (UV) block.

While particular embodiments of the invention have been illustrated and described in detail herein, it should be understood that various changes and modifications may be made to the invention without departing from the spirit and intent of the invention as defined by the scope of the appended claims.

What is claimed is:

1. A method of producing a tattoo that is not visible to the naked eye until the tattoo is exposed to ultraviolet radiation, comprising the steps of:

providing a colorless carrier suitable for embedding in the skin of a human;

mixing in the carrier one or more photochromic compounds that appear colorless and are invisible to the naked eye until exposed to ultraviolet radiation, and which undergo a photochemical transformation from colorless to colored upon exposure to ultraviolet radiation, thereby becoming visible to the naked eye, and which revert to colorless following elapse of a predetermined interval of time upon removal from exposure to ultraviolet radiation, thereby becoming visible to the naked eye; and embedding the mixture of carrier and photochromic compound transdermally in the skin of a human to form a tattoo.

2. A method as claimed in claim 1, wherein:
   the mixture of carrier and photochromic compound is applied transdermally to the skin using conventional tattooing methods.

3. A method as claimed in claim 1, wherein:
   the photochromic compounds are selected from the family of spiropyrans and spiroxazines groups of molecules.

4. A method as claimed in claim 1, wherein:
   the carrier is an invisible skin marking ink.

5. A method as claimed in claim 2, wherein:
   the photochromic compounds are selected from the family of spiropyrans and spiroxazines groups of molecules.

6. A method as claimed in claim 5, wherein:
   the carrier is an invisible skin marking ink.

* * * * *